(12) United States Patent
Fillatti

(10) Patent No.: US 7,256,329 B2
(45) Date of Patent: Aug. 14, 2007

(54) NUCLEIC ACID SEQUENCES AND METHODS OF USE FOR THE PRODUCTION OF PLANTS WITH MODIFIED POLYUNSATURATED FATTY ACIDS

(75) Inventor: Joanne Fillatti, Davis, CA (US)

(73) Assignee: Calgene LLC, Davis, CA (US)

( * ) Notice: Subject to any disclaimer, the term of this patent is extended or adjusted under 35 U.S.C. 154(b) by 612 days.

(21) Appl. No.: 10/606,772

(22) Filed: Jun. 27, 2003

(65) Prior Publication Data
US 2004/0098762 A1    May 20, 2004

Related U.S. Application Data

(63) Continuation of application No. 09/638,508, filed on Aug. 11, 2000, now abandoned.

(60) Provisional application No. 60/172,128, filed on Dec. 17, 1999, provisional application No. 60/151,224, filed on Aug. 26, 1999.

(51) Int. Cl.
*A01H 5/00* (2006.01)
*C12N 15/82* (2006.01)
(52) U.S. Cl. .................... 800/312; 435/415
(58) Field of Classification Search .............. None
See application file for complete search history.

(56) References Cited

U.S. PATENT DOCUMENTS

| | | | |
|---|---|---|---|
| 4,557,734 | A | 12/1985 | Schwab et al. |
| 5,454,842 | A | 10/1995 | Poirier et al. |
| 5,475,099 | A | 12/1995 | Knauf et al. |
| 5,500,361 | A | 3/1996 | Kinney |
| 5,627,061 | A | 5/1997 | Barry et al. |
| 5,633,435 | A | 5/1997 | Barry et al. |
| 5,714,670 | A | 2/1998 | Fehr et al. |
| 5,723,595 | A | 3/1998 | Thompson et al. |
| 5,723,761 | A | 3/1998 | Voelker et al. |
| 5,850,026 | A | 12/1998 | DeBonti et al. |
| 5,888,947 | A | 3/1999 | Lambert et al. |
| 5,891,203 | A | 4/1999 | Ball et al. |
| 5,955,329 | A | 9/1999 | Yuan et al. |
| 5,955,650 | A | 9/1999 | Hitz |
| 6,013,114 | A | 1/2000 | Hille et al. |
| 6,150,512 | A | 11/2000 | Yuan |
| 6,331,664 | B1 | 12/2001 | Rubin-Wilson et al. |
| 6,369,296 | B1 | 4/2002 | Ratcliff et al. |
| 6,372,965 | B1 | 4/2002 | Lightner et al. |
| 6,380,462 | B1 | 4/2002 | Kridl |
| 6,506,559 | B1 | 1/2003 | Fire et al. |
| 6,573,099 | B2 | 6/2003 | Graham |
| 2002/0034814 | A1 | 3/2002 | Atabekov et al. |
| 2003/0049835 | A1 | 3/2003 | Helliwell et al. |
| 2003/0135882 | A1 | 7/2003 | Metzlaff et al. |
| 2003/0172399 | A1 | 9/2003 | Fillatti |
| 2004/0107460 | A1 | 6/2004 | Fillatti et al. |
| 2004/0126845 | A1 | 7/2004 | Eenennaam et al. |
| 2005/0034190 | A9 | 2/2005 | Fillatti et al. |

FOREIGN PATENT DOCUMENTS

| | | |
|---|---|---|
| EP | 0 959 133 A1 | 11/1999 |
| WO | WO 93/11245 A1 | 6/1993 |
| WO | WO 94/10189 A1 | 5/1994 |
| WO | WO 94/11516 A1 | 5/1994 |
| WO | WO 96/06936 | 3/1996 |
| WO | WO 98/05770 A2 | 2/1998 |
| WO | WO 98/30083 A1 | 7/1998 |
| WO | WO 98/46776 A2 | 10/1998 |
| WO | WO 98/53083 A1 | 11/1998 |
| WO | WO 99/15682 A2 | 4/1999 |
| WO | WO 99/32619 A1 | 7/1999 |
| WO | WO 99/49029 A1 | 9/1999 |
| WO | WO 99/53050 A1 | 10/1999 |
| WO | WO 99/61631 A1 | 12/1999 |
| WO | WO 99/64579 A2 | 12/1999 |
| WO | WO 00/07432 A1 | 2/2000 |
| WO | WO 00/18880 | 4/2000 |
| WO | WO 00/44895 A1 | 8/2000 |
| WO | WO 00/44914 A1 | 8/2000 |
| WO | WO 00/68374 A1 | 11/2000 |
| WO | WO 01/11061 | 2/2001 |
| WO | WO 01/14538 A2 | 3/2001 |
| WO | WO 01/34822 A2 | 5/2001 |
| WO | WO 01/35726 A1 | 5/2001 |
| WO | WO 01/36598 A1 | 5/2001 |
| WO | WO 01/70949 A1 | 9/2001 |
| WO | WO 01/79499 A1 | 10/2001 |
| WO | WO 02/04581 A1 | 1/2002 |
| WO | WO 02/15675 A1 | 2/2002 |
| WO | WO 02/059336 A2 | 8/2002 |
| WO | WO 02/081711 A1 | 10/2002 |
| WO | WO 02/088301 A2 | 11/2002 |
| WO | WO 03/080802 A2 | 10/2003 |

OTHER PUBLICATIONS

De Luca, V. AgBiotech News and Information 5 (6):225N-229N, 1993.*
Cartea et al., "Comparison of Sense and Antisense Methodologies for Modifying the Fatty Acid Composition of *Arabidopsis Thaliana* Oilseed," *Plant Science*, 136:181-194 (1998).

(Continued)

*Primary Examiner*—Elizabeth F. McElwain
(74) *Attorney, Agent, or Firm*—Chunping Li; Arnold & Porter LLP

(57) ABSTRACT

By this invention, novel nucleic acid sequences are provided, wherein said nucleic acid sequence is a genomic sequence of a plant desaturase encoding sequence. Also provided in the present invention are the promoter and intron sequences of the desaturase genomic sequences. Furthermore, recombinant DNA constructs employing the polynucleotide sequences are provided. The instant invention also provides methods for the modification of fatty acid compositions in host plant cells.

24 Claims, No Drawings

OTHER PUBLICATIONS

Clark-Walker et al., "Location of Transcriptional Control Signals and Transfer RNA Sequences in *Torulopsis-Glabrata* Mitochondrial DNA," *EMBO Journal*, 4(2):465-473 (1985).

EMBL/Genbank, AC AL069706, "*Drosophila melanogaster* genome survey sequence T7 end of BAC: BACR29B23 of RPCI-98 library from *Drosophila melanogaster* (fruit fly)," Abst. (May 29, 1999).

EMBL/Genbank, AC AL071390, "*Drosophila melanogaster* genome survey sequence TET3 end of BAC: BACR32M05," Abst. (May 29, 1999).

EMBL/Genbank, AC AL105179, "*Drosophila melanogaster* genome survey sequence T7 end of BAC: BACN13A12 of DrosBAC library from *Drosophila melanogaster* (fruit fly)," Abst. (Jul. 26, 1999).

EMBL/Genbank, AC AL108811, "*Drosophila melanogaster* genome survey sequence SP6 end of BAC: BACN37D10 of DrosBAC library from *Drosophila malanogaster* (fruit fly)," Abst. (Jul. 26, 1999).

EMBL/Genbank, AC AL063932, "*Drosophila melanogaster* genome survey sequence TET3 end of BAC: BACR08010 of RPCI-98 library from *Drosophila melanogaster* (fruit fly)," Abst. (May 29, 1999).

EMBL/Genbank, AC AC004705, "*Arabidopsis thaliana* chromosome II section 85 of 255 of the complete sequence. Sequence from clones F26C24, T26I20," Abst. (May 21, 1998).

EMBL/Genbank, AC AB0222220, *Arabidopsis thaliana* genomic DNA, chromosome 3, PI clone: MLN21, Abst. (Jan. 15, 1999).

EMBL/Genbank, AC AB026636, "*Arabidopsis thaliana* genomic DNA, chromosome 3, TAC clone: K14A17," Abst. (May 7, 1999).

EMBL/Genbank, AC AW397948, "sg70c08.yl Gm-c1007 Glycine max cDNA clone Genome Systems Clone ID: Gm-c1007-1767 5' similar to SW:FD61-SOYBN P48630 Omega-6 Fatty Acid Desaturase, Endoplasmic Reticulum Isozyme 1; mRNA sequence," Abst. (Feb. 8, 2000).

EMBL/Genbank, AC AL161581, "*Arabidopsis thaliana* DNA chromosome 4, contig fragment No. 77," Abst. (Mar. 16, 2000).

International Search Report, International Application No. PCT/US00/22613, 5 pages (mailed Apr. 26, 2001).

Lewin, "How did interrupted genes evolve," *Genes*, 2nd ed., John Wiley & Sons, New York, pp. 333-387 (1983).

Okuley et al., "*Arabidopsis* FAD2 Gene Encodes the Enzyme that is Essential for Polyunsaturated Lipid Synthesis," *The Plant Cell*, 6:147-158 (Jan. 1994).

Liu, Thesis, University of Sydney, Australia, pp. ii-iv, 24-26, 121-123, 142, 167, 168, 172-174, 179-181 (Mar. 1998).

Bouchon, p. et al., "Oil Distribution in Fried Potatoes Monitored by Infrared Microspectroscopy", *Journal of Food Science*, 66(7):918-923 (2001).

Buhr, T. et al., "Ribozyme Termination of RNA Transcripts Down-Regulate Seed Fatty Acid Genes in Transgenic Soybean", *The Plant Journal*, 30(2):155-163 (2002).

Cogoni, C. et al., "Post-Transcriptional Gene Silencing Across Kingdoms", *Curr. Opin. Gen. & Devel.*, 10(6):638-643 (2000).

Crossway, A. et al., "Integration of Foreign DNA Following Microinjection of Tobacco Mesophyll Protoplasts", *Mol. Gen. Genet.*, 202(2):179-185 (1986).

Dörmann, P. et al., "Accumulation of Palmitate in *Arabidopsis* Mediated by the Acyl-Acyl Carrier Protein Thioesterase FATBI", *Plant Physiology*, 123:637-643 (2000).

Duffield, J. et al., "U.S. Biodiesel Development: New Markets for Conventional and Genetically Modified Agricultural Products", *Economic Research Service USDA*, pp. 1-31 (1998).

Dunn, R. et al., "Recent Advances in the Development of Alternative Diesel Fuel from Vegetable Oils and Animal Fats", *Recent Res. Devel. in Oil Chem.*, 1:31-56 (1997).

Erhan, S. et al., "Lubricant Basestocks from Vegetable Oils", *Industrial Crops and Products*, 11:277-282 (2000).

Fire, A. et al., "Potent and Specific Genetic Interference by Double-Stranded RNA in *Caenorhabditis elegans*", *Nature*, 391:806-811 (1998).

Halpin, C. et al., "Enabling Technologies for Manipulating Multiple Genes on Complex Pathways", *Plant Molecular Biology*, 47:295-310 (2001).

Hamada, T. et al., "Modification of Fatty Acid Composition by Over- and Antisense-Expression of a Microsomal $\omega$-3 Fatty Acid Desaturase Gene in Transgenic Tobacco", *Transgenic Research*, 5(2), 115-121 (1996).

International Search Report dated Nov. 13, 2003 in PCT/US03/08610.

International Search Report dated Jul. 12, 2005, issued in PCT/US04/31605.

International Search Report dated Apr. 9, 2004, issued in PCT/US03/19445.

Lee, Y., et al., "Antisense Expression of the CK2 $\alpha$-Subunit Gene in *Arabidopsis*. Effects on Light-Regulated Gene Expression and Plant Growth", *Plant Physiology*, 119:989-1000 (1999).

Matzke, M.A. et al., "RNA-Based Silencing Strategies in Plants", *Curr. Opin. Gen. & Devel.*, 11(2):221-227 (2001).

Mensink, R. et al., "Effect of Dietary Fatty Acids on Serum Lipids and Lipoproteins: A Meta-Analysis of 27 Trials", *Arteriosclerosis and Thrombosis*, 12(8):911-919 (1992).

Montgomery, M.K. et al., "RNA as a Target of Double-Stranded RNA-Mediated Genetic Interference in *Caenorhabditis elegans*", *Proc. Natl. Acad. Sci. USA*, 95(96):15502-15507 (1998).

Napoli, C. et al., "Introduction of Chimeric Chalcone Synthase Gene into Petunia Results in Reversible Co-Suppression of Homologous Genes *in trans*", *The Plant Cell*, 2:279-289 (1990).

Neff, W.E. et al., "Odor Significance of Undersirable Degradation Compounds in Heated Triolein and Trilinolein", *JAOCS*, 77(12):1303-1313 (2000).

Sharp, P.A., "RNAi and Double-Strand RNA", *Genes & Development*, 13:139-141 (1999).

Sharp, P.A., "RNA Interference—2001", *Genes & Development*, 15:485-490 (2001).

Supplemental European Search Report in European Application No. 03711656.3 completed Jun. 29, 2005.

Timmons, J.S. et al., "Relationships Among Dietary Roasted Soybeans, Milk Components, and Spontaneous Oxidized Flavor of Milk", *Journal of Diary Science*, 84(11):2440-2449 (2001).

Toborek, M. et al., "Unsaturated Fatty Acids Selectively Induce an Inflammatory Environment in Human Endothelial Cells", *American Journal of Clinical Nutrition*, 75:119-125 (2002).

van der Krol, A. R. et al., "Flavonoid Genes in Petunia: Addition of a Limited Number of Gene Copies May Lead to a Suppression of Gene Expression", *The Plant Cell*, 2:291-299 (1990).

Warner, K. et al., "Effect of Oleic and Linoleic Acids on the Production of Deep-Fried Odor in Heated Triolein and Trilinolein", *Journal of Agricultural Food Chemical*, 49:899-905 (2001).

Waterhouse, P.M. et al., "Virus Resistance and Gene Silencing in Plants Can be Induced by Simultaneous Expression of Sense and Antisense RNA", *Proc. Natl. Acad. Sci. USA*, 95:13959-13964 (1998).

Wesley, S.V. et al., "Construct Design for Efficient, Effective and High-Throughput Gene Silencing in Plants", *The Plant Journal*, 27(6):581-590 (2001).

Bosher et al., "RNA Interference Can Target Pre-mRNA: Consequences for Gene Expression in a *Caenorhabditis elegans* Operon", *Genetics*, 153:1245-1256 (1999).

Chuang et al., "Specific and Heritable Genetic Interference by Double-Stranded RNA in *Arabidopsis Thaliana*", *PNAS*, 97(9):4985-4990 (2000).

Colliver et al., "Differential modification of flavonoid and isoflavonoid biosynthesis with an antisense chalcone synthase construct in transgnic *Lotus corniculatus*", Plant Mol. Biol., 35:509-522 (1997).

Hamilton et al., "A Transgene with Repeated DNA Causes High Frequency, Post-Transcriptional Suppression of ACC-Oxidase Gene Expression in Tomato", *The Plant Journal*, 15(6):737-746 (1998).

International Search Report of International Application No. PCT/US2003/019437 dated Jun. 21, 2004.

Jaworski et al., "Industrial oils from transgenic plants", *Current Opinion in Plant Biology*, 6:178-184 (2003).

Padgette et al., "Development, Identification, and Characterization of a Glyphosate-Tolerant Soybean Line", *Crop Sci.*, 35:1451-1461 (1995).

Qing, L., Thesis, "The Isolation and Characterisation of Fatty Acid Desaturase Genes in Cotton", University of Sydney, Australia, pp. ii-iv, 24-26, 121-123, 142, 167-168, 172-174, 179-181 (1998).

Singh et al., "Metabolic engineering of new fatty acids in plants", *Current Opinion in Plant Biology*, 8:197-203 (2005).

Smith et al., "Total silencing by intron-spliced hairpin RNAs", *Nature*, 407:319-320 (2000).

Stam et al., "Post-transcriptional silencing of chalcone synthase in *Petunia* by inverted transgene repeats", *The Plant Journal* 12(1):63-82 (1997).

Stoutjesdijk et al., "hpRNA-Mediated Targeting of the *Arabidopsis* FAD 2 Gene Gives Highly Efficient and Stable Silencing", *Plant Physiology*, 129:1723-1731 (2002).

Supplementary Partial European Search Report in Application No. 03 76 1158 dated Jan. 8, 2007.

Levin et al., "Methods of double-standed RNA-mediated gene inactivation in *Arabidopsis* and their use to define an essential gene in methionine biosynthesis," *Plant Molecular Biology*, 44(6):759-775 (2000).

Peele et al., "Silencing of a meristematic gene using geminivirus-derived vectors," *The Plant Journal*, 2(4):357-366 (2001).

Supplementary European Search Report, European Application No. 04 78 5109 (Nov. 7, 2006).

\* cited by examiner

SEQUENCE LISTING

```
<160> NUMBER OF SEQ ID NOS: 33

<210> SEQ ID NO 1
<211> LENGTH: 4497
<212> TYPE: DNA
<213> ORGANISM: Glycine max

<400> SEQUENCE: 1
cttgcttggt aacaacgtcg tcaagttatt attttgttct ttttttttt atcatatttc      60 ttattttgtt ccaagtatgt catattttga tccatcttga caagtagatt gtcatgtagg    120
aataggaata tcactttaaa ttttaaagca ttgattagtc tgtaggcaat attgtcttct    180
tcttcctcct tattaatatt ttttattctg ccttcaatca ccagttatgg gagatggatg    240
taatactaaa taccatagtt gttctgcttg aagtttagtt gtatagttgt tctgcttgaa    300
gtttagttgt gtgtaatgtt tcagcgttgg cttcccctgt aactgctaca atggtactga    360
atatatattt tttgcattgt tcattttttt cttttactta atcttcattg ctttgaaatt    420
aataaaacaa aaagaaggac cgaatagttt gaagtttgaa ctattgccta ttcatgtaac    480
ttattcaccc aatcttatat agttttttctg gtagagatca ttttaaattg aaggatataa    540
attaagagga aatacttgta tgtgatgtgt ggcaatttgg aagatcatgc gtagagagtt    600
taatggcagg ttttgcaaat tgacctgtag tcataattac actgggccct ctcggagttt    660
tgtgcctttt tgttgtcgct gtgtttggtt ctgcatgtta gcctcacaca gatatttagt    720
agttgttgtt ctgcatataa gcctcacacg tatactaaac gagtgaacct caaaatcatg    780
gccttacacc tattgagtga aattaatgaa cagtgcatgt gagtatgtga ctgtgacaca    840
acccccggtt tcatattgc aatgtgctac tgtggtgatt aaccttgcta cactgtcgtc    900
cttgtttgtt tccttatgta tattgatacc ataaattatt actagtatat catttttatat    960 tgtccatacc attacgtgtt tatagtctct ttatgacatg taattgaatt ttttaattat   1020
```

-continued

```
aaaaaataat aaaacttaat tacgtactat aaagagatgc tcttgactag aattgtgatc    1080
tcctagtttc ctaaccatat actaatattt gcttgtattg atagcccctc cgttcccaag    1140
agtataaaac tgcatcgaat aatacaagcc actaggcatg gtaaattaaa ttgtgcctgc    1200
acctcgggat atttcatgtg gggttcatca tatttgttga ggaaaagaaa ctcccgaaat    1260
tgaattatgc atttatatat cctttttcat ttctagattt cctgaaggct taggtgtagg    1320
cacctagcta gtagctacaa tatcagcact tctctctatt gataaacaat tggctgtaat    1380
gccgcagtag aggacgatca caacatttcg tgctggttac tttttgtttt atggtcatga    1440
tttcactctc tctaatctct ccattcattt tgtagttgtc attatcttta gatttttcac    1500
tacctggttt aaaattgagg gattgtagtt ctgttggtac atattacaca ttcagcaaaa    1560
caactgaaac tcaactgaac ttgtttatac tttgacacag ggtctagcaa aggaaacaac    1620
aatgggaggt agaggtcgtg tggcaaagtg gaagttcaag ggaagaagcc tctctcaagg    1680
gttccaaaca caaagccacc attcactgtt ggccaactca agaaagcaat tccaccacac    1740
tgctttcagc gctccctcct cacttcattc tcctatgttg tttatgacct ttcatttgcc    1800
ttcattttct acattgccac cacctacttc cacctccttc ctcaacccttt ttccctcatt    1860
gcatggccaa tctattgggt tctccaaggt tgccttctca ctggtgtgtg ggtgattgct    1920
cacgagtgtg gtcaccatgc cttcagcaag taccaatggg ttgatgatgt tgtgggtttg    1980
acccttcact caaacttttt agtcccttat ttctcatgga aaataagcca tcgccgccat    2040
cactccaaca caggttccct tgaccgtgat gaagtgtttg tcccaaaacc aaaatccaaa    2100
gttgcatggt tttccaagta cttaaacaac cctctaggaa gggctgtttc tcttctcgtc    2160
acactccacaa taggtggcc tatgtattta gccttcaatg tctctggtag acccctatgat    2220
agttttgcaa gccactacca cccttatgct cccatatatt ctaaccgtga gaggcttctg    2280
atctatgtct ctgatgttgc tttgttttct gtgacttact ctctctaccg tgttgcaacc    2340
ctgaaagggt tggtttggct gctatgtgtt tatggggtgc cttttgctcat tgtgaacggt    2400
tttcttgtga ctatcacata tttgcagcac acacactttg ccttgcctca ttacgattca    2460
tcagaatggg actggctgaa gggagctttg gcaactatgg acagagatta tgggattctg    2520
aacaaggtgt ttcatcacat aactgatact catgtggctc accatctctt ctctacaatg    2580
ccacattacc atgcaatgga ggcaaccaat gcaatcaagc caatattggg tgagtactac    2640
caatttgatg acacaccatt ttacaaggca ctgtggagag aagcgagaga gtgcctctat    2700
gtggagccag atgaaggaac atccgagaag ggcgtgtatt ggtacaggaa caagtattga    2760
tggagcaacc aatgggccat agtgggagtt atggaagttt tgtcatgtat tagtacataa    2820
ttagtagaat gttataaata agtggatttg ccgcgtaatg actttgtgtg tattgtgaaa    2880
cagcttgttg cgatcatggt tataatgtaa aaataattct ggtattaatt acatgtggaa    2940
agtgttctgc ttatagcttt ctgcctaaaa tgcacgctgc acgggacaat atcattggta    3000
attttttttaa aatctgaatt gaggctactc ataatactat ccataggaca tcaaagacat    3060
gttgcattga ctttaagcag aggttcatct agaggattac tgcataggct tgaactacaa    3120
gtaatttaag ggacgagagc aactttagct ctaccacgtc gttttacaag gttattaaaa    3180
tcaaattgat cttattaaaa ctgaaaattt gtaataaaat gctattgaaa aattaaaata    3240
tagcaaacac ctaaattgga ctgattttta gattcaaatt taataattaa tctaaattaa    3300
acttaaatttt tataatatat gtcttgtaat atatcaagtt ttttttttta ttattgagtt    3360
```

```
tggaaacata taataaggaa cattagttaa tattgataat ccactaagat cgacttagta    3420
ttacagtatt tggatgattt gtatgagata ttcaaacttc actcttatca taatagagac    3480
aaaagttaat actgatggtg gagaaaaaaa aatgttattg ggagcatatg gtaagataag    3540
acggataaaa atatgctgca gcctggagag ctaatgtatt ttttggtgaa gttttcaagt    3600
gacaactatt catgatgaga acacaataat attttctact tacctatccc acataaaata    3660
ctgattttaa taatgatgat aaataatgat taaaatattt gattctttgt taagagaaat    3720
aaggaaaaca taaatattct catggaaaaa tcagcttgta ggagtagaaa ctttctgatt    3780
ataattttaa tcaagtttaa ttcattcttt taatttatt attagtacaa aatcattctc    3840
ttgaatttag agatgtatgt tgtagcttaa tagtaatttt ttatttttat aataaaattc    3900
aagcagtcaa atttcatcca ataatcgtg ttcgtgggtg taagtcagtt attccttctt    3960
atcttaatat acacgcaaag gaaaaaataa aaataaaatt cgaggaagcg cagcagcagc    4020
tgataccacg ttggttgacg aaactgataa aaagcgctgt cattgtgtct ttgtttgatc    4080
atcttcacaa tcacatctcc agaacacaaa gaagagtgac ccttcttctt gttattccac    4140
ttgcgttagg tttctacttt cttctctctc tctctctc tcttcattcc tcattttcc    4200 ctcaaacaat caatcaattt tcattcagat tcgtaaattt ctcgattaga tcacggggtt    4260
aggtctccca ctttatcttt tcccaagcct ttctctttcc cctttccct gtctgcccca    4320 taaaattcag gatcggaaac gaactggggtt cttgaatttc actctagatt ttgacaaatt    4380
cgaagtgtgc atgcactgat gcgacccact ccccctttt tgcattaaac aattatgaat    4440
tgaggttttt cttgcgatca tcattgcttg aattgaatca tattaggttt agattct       4497

<210> SEQ ID NO 2
<211> LENGTH: 420
<212> TYPE: DNA
<213> ORGANISM: Glycine max

<400> SEQUENCE: 2
gtaaattaaa ttgtgcctgc acctcgggat atttcatgtg gggttcatca tatttgttga     60
ggaaaagaaa ctcccgaaat tgaattatgc atttatatat ccttttcat ttctagattt     120 cctgaaggct taggtgtagg cacctagcta gtagctacaa tatcagcact tctctctatt    180
gataaacaat tggctgtaat gccgcagtag aggacgatca caacatttcg tgctggttac    240 ttttttgtttt atggtcatga tttcactctc tctaatctct ccattcattt tgtagttgtc    300
attatcttta gattttttcac tacctggttt aaaattgagg gattgtagtt ctgttggtac    360
atattacaca ttcagcaaaa caactgaaac tcaactgaac ttgtttatac tttgacacag    420

<210> SEQ ID NO 3
<211> LENGTH: 4010
<212> TYPE: DNA
<213> ORGANISM: Glycine max

<400> SEQUENCE: 3
acaaagcctt tagcctatgc tgccaataat ggataccaac aaaagggttc ttcttttgat     60
tttgatccta gcgctcctcc accgtttaag attgcagaaa tcagagcttc aataccaaaa    120
cattgctggg tcaagaatcc atggagatcc ctcagttatg ttctcaggga tgtgcttgta    180
attgctgcat tggtggctgc agcaattcac ttcgacaact ggcttctctg gctaatctat    240
tgccccattc aaggcacaat gttctgggct ctctttgttc ttggacatga ttggtaataa    300
tttttgtgtt tcttactctt ttttttttt ttttgtttat gatatgaatc tcacacattg    360
```

```
ttctgttatg tcatttcttc ttcatttggc tttagacaac ttaaatttga gatctttatt      420
atgttttgc ttatatggta aagtgattct tcattatttc attcttcatt gattgaattg       480
aacagtggcc atggaagctt ttcagatagc cctttgctga atagcctggt gggacacatc      540
ttgcattcct caattcttgt gccataccat ggatggttag ttcatactgg ctttttttgtt     600
tgttcatttg tcattgaaaa aaaatctttt gttgattcaa ttatttttat agtgtgtttg      660
gaagcccgtt tgagaaaata agaaatcgca tctggaatgt gaaagttata actatttagc      720
ttcatctgtc gttgcaagtt cttttattgg ttaaattttt atagcgtgct aggaaaccca      780
ttcgagaaaa taagaaatca catctggaat gtgaaagtta taactgttag cttctgagta      840
aacgtggaaa aaccacattt tggatttgga accaaatttt atttgataaa tgacaaccaa      900
attgattttg atggattttg caggagaatt agccacagaa ctcaccatga aaccatgga       960
cacattgaga aggatgagtc atgggttcca gtatgtgatt aattgcttct cctatagttg     1020
ttcttgattc aattacattt tatttatttg gtaggtccaa gaaaaaggg aatctttatg      1080
cttcctgagg ctgttcttga acatggctct tttttatgtg tcattatctt agttaacaga     1140
gaagatttac aagaatctag acagcatgac aagactcatt agattcactg tgccatttcc     1200
atgtttgtgt atccaatta tttggtgagt gattttttga cttggaagac aacaacacat      1260
tattattata atatggttca aaacaatgac ttttttcttta tgatgtgaac tccatttttt    1320
agttttcaag aagccccgga aaggaaggct ctcacttcaa tccctacagc aatctgtttc     1380
cacccagtga gagaaaagga atagcaatat caacactgtg ttgggctacc atgttttctc     1440
tgcttatcta tctctcattc attaactagt ccacttctag tgctcaagct ctatggaatt     1500
ccatattggg taactaaatt actcctacat tgttactttt tcctccttt ttttattatt      1560
tcaattctcc aattggaaat ttgaaatagt taccataatt atgtaattgt ttgatcatgt     1620
gcagatgttt gttatgtggc tggactttgt cacatacttg catcaccatg gtcaccacca     1680
gaaactgcct tggtaccgcg gcaaggtaac aaaaataaat agaaaatagt gggtgaacac     1740
ttaaatgcga gatagtaata cctaaaaaaa gaaaaaaata taggtataat aaataatata    1800
actttcaaaa taaaagaaa tcatagagtc tagcgtagtg tttggagtga atgatgttc       1860
acctaccatt actcaaagat tttgttgtgt cccttagttc attcttatta ttttacatat     1920
cttacttgaa aagactttt aattattcat tgagatctta aagtgactgt taaattaaaa      1980
taaaaacaa gtttgttaaa acttcaaata aataagagtg aagggagtgt catttgtctt     2040
ctttctttta ttgcgttatt aatcacgttt ctcttctctt tttttttttt cttctctgct    2100
ttccacccat tatcaagttc atgtgaagca gtggcggatc tatgtaaatg agtgggggc     2160
aattgcaccc acaagatttt attttttatt tgtacaggaa taataaaata aactttgcc    2220
cccataaaaa ataaatattt tttcttaaaa taatgcaaaa taaatataag aaataaaaag    2280
agaataaatt attattaatt ttattatttt gtacttttta tttagttttt ttagcggtta    2340
gattttttt tcatgacatt atgtaatctt ttaaaagcat gtaatatttt tattttgtga    2400
aaataaatat aaatgatcat attagtctca gaatgtataa actaataata attttatcac    2460
taaaagaaat tctaatttag tccataaata agtaaaacaa gtgacaatta tattttatat    2520
ttacttaatg tgaaataata cttgaacatt ataataaaac ttaatgacag gagatattac    2580
atagtgccat aaagatattt taaaaaataa aatcattaat acactgtact actatataat    2640
attcgatata tattttttaac atgattctca atagaaaaat tgtattgatt atattttatt   2700
```

-continued

```
agacatgaat ttacaagccc cgttttttcat ttatagctct tacctgtgat ctattgtttt      2760
gcttcgctgt ttttgttggt caagggactt agatgtcaca atattaatac tagaagtaaa      2820
tatttatgaa aacatgtacc ttacctcaac aaagaaagtg tggtaagtgg caacacacgt      2880
gttgcatttt tggcccagca ataacacgtg ttttttgtggt gtactaaaat ggacaggaat     2940
ggagttattt aagaggtggc ctcaccactg tggatcgtga ctatggttgg atcaataaca      3000
ttcaccatga cattggcacc catgttatcc accatctttt cccccaaatt cctcattatc      3060
acctcgttga agcggtacat tttattgctt attcacctaa aaacaataca attagtacat      3120
ttgttttatc tcttggaagt tagtcatttt cagttgcatg attctaatgc tctctccatt      3180
cttaaatcat gttttcacac ccacttcatt taaaataaga acgtgggtgt tattttaatt      3240
tctattcact aacatgagaa attaacttat ttcaagtaat aattttaaaa tattttatg       3300 ctattatttt attacaaata attatgtata ttaagtttat tgattttata ataattatat     3360
taaaattata tcgatattaa tttttgattc actgatagtg ttttatattg ttagtactgt     3420
gcatttattt taaaattggc ataaataata tatgtaacca gctcactata ctatactggg     3480
agcttggtgg tgaaaggggt tcccaacccct cctttctagg tgtacatgct ttgatacttc    3540
tggtaccttc ttatatcaat ataaattata ttttgctgat aaaaaaacat ggttaaccat     3600
taaattcttt ttttaaaaaa aaaactgtat ctaaactttg tattattaaa aagaagtctg    3660
agattaacaa taaactaaca ctcatttgga ttcactgcag acacaagcag caaaaccagt     3720
tcttggagat tactaccgtg agccagaaag atctcgcgcca ttaccatttc atctaataaa    3780
gtatttaatt cagagtatga gacaagacca cttcgtaagt gacactggag atgttgttta    3840
ttatcagact gattctctgc tcctccactc gcaacgagac tgagtttcaa acttttttggg   3900 ttattattta ttgattctag ctactcaaat tactttttttt ttaatgttat gttttttgga   3960
gtttaacgtt ttctgaacaa cttgcaaatt acttgcatag agagacatgg                4010
```

```
<210> SEQ ID NO 4
<211> LENGTH: 192
<212> TYPE: DNA
<213> ORGANISM: Glycine max

<400> SEQUENCE: 4
```

```
gtaataattt ttgtgtttct tactcttttt tttttttttt tgtttatgat atgaatctca      60
cacattgttc tgttatgtca tttcttcttc atttggcttt agacaactta aatttgagat     120
ctttattatg ttttttgctta tatggtaaag tgattcttca ttatttcatt cttcattgat    180
tgaattgaac ag                                                         192
```

```
<210> SEQ ID NO 5
<211> LENGTH: 348
<212> TYPE: DNA
<213> ORGANISM: Glycine max

<400> SEQUENCE: 5
```

```
gttagttcat actggctttt ttgtttgttc atttgtcatt gaaaaaaat cttttgttga       60 ttcaattatt tttatagtgt gtttggaagc ccgtttgaga aaataagaaa tcgcatctgg     120
aatgtgaaag ttataactat ttagcttcat ctgtcgttgc aagttctttt attggttaaa    180
tttttatagc gtgctaggaa acccattcga gaaataaga aatcacatct ggaatgtgaa     240
agttataact gttagcttct gagtaaacgt ggaaaaacca catttggat ttggaaccaa     300 attttatttg ataaatgaca accaaattga ttttgatgga ttttgcag                 348
```

<210> SEQ ID NO 6
<211> LENGTH: 142
<212> TYPE: DNA
<213> ORGANISM: Glycine max

<400> SEQUENCE: 6

```
gtatgtgatt aattgcttct cctatagttg ttcttgattc aattcactttt tatttatttg    60
gtaggtccaa gaaaaaaggg aatctttatg cttcctgagg ctgttcttga acatggctct   120
tttttatgtg tcattatctt ag                                            142
```

<210> SEQ ID NO 7
<211> LENGTH: 1231
<212> TYPE: DNA
<213> ORGANISM: Glycine max

<400> SEQUENCE: 7

```
gtaacaaaaa taaatagaaa atagtgggtg aacacttaaa tgcgagatag taatacctaa    60
aaaaagaaaa aaatataggt ataataaata atataacttt caaaataaaa agaaatcata   120
gagtctagcg tagtgtttgg agtgaaatga tgttcaccta ccattactca aagattttgt   180
tgtgtccctt agttcattct tattatttta catatcttac ttgaaaagac tttttaatta   240
ttcattgaga tcttaaagtg actgttaaat taaaataaaa aacaagtttg ttaaaacttc   300
aaataaataa gagtgaaggg agtgtcattt gtcttctttc ttttattgcg ttattaatca   360
cgtttctctt ctcttttttt tttttcttct ctgctttcca cccattatca agttcatgtg   420
aagcagtggc ggatctatgt aaatgagtgg ggggcaattg cacccacaag attttatttt   480
ttatttgtac aggaataata aaataaaact ttgcccccat aaaaaataaa tattttttct   540
taaaataatg caaaataaat ataagaaata aaaagagaat aaattattat taattttatt   600
attttgtact tttttatttag tttttttagc ggttagattt ttttttcatg acattatgta   660
atcttttaaa agcatgtaat attttttattt tgtgaaaata aatataaatg atcatattag   720
tctcagaatg tataaactaa taataatttt atcactaaaa gaaattctaa tttagtccat   780
aaataagtaa aacaagtgac aattatattt tatatttact taatgtgaaa taatacttga   840
acattataat aaaacttaat gacaggagat attacatagt gccataaaga tattttaaaa   900
aataaaatca ttaatacact gtactactat ataatattcg atatatattt taacatgat   960
tctcaataga aaaattgtat tgattatatt ttattagaca tgaatttaca agccccgttt  1020
ttcattata gctcttacct gtgatctatt gttttgcttc gctgtttttg ttggtcaagg  1080
gacttagatg tcacaatatt aatactagaa gtaaatattt atgaaaacat gtaccttacc  1140
tcaacaaaga aagtgtggta agtggcaaca cacgtgttgc atttttggcc cagcaataac  1200
acgtgttttt gtggtgtact aaaatggaca g                                 1231
```

<210> SEQ ID NO 8
<211> LENGTH: 626
<212> TYPE: DNA
<213> ORGANISM: Glycine max

<400> SEQUENCE: 8

```
gtacattttta ttgcttattc acctaaaaac aatacaatta gtacatttgt tttatctctt    60
ggaagttagt cattttcagt tgcatgattc taatgctctc tccattctta aatcatgttt   120
tcacacccac ttcatttaaa ataagaacgt gggtgttatt ttaatttcta ttcactaaca   180
```

```
tgagaaatta acttatttca agtaataatt ttaaaatatt ttttatgctat tattttatta        240 caaataatta tgtatattaa gtttattgat tttataataa ttatattaaa attatatcga        300 tattaattt tgattcactg atagtgtttt atattgttag tactgtgcat ttattttaaa         360
attggcataa ataatatatg taaccagctc actatactat actgggagct tggtggtgaa        420
aggggttccc aaccctcctt tctaggtgta catgctttga tacttctggt accttcttat        480
atcaatataa attatatttt gctgataaaa aaacatggtt aaccattaaa ttcttttttt        540
aaaaaaaaaa ctgtatctaa actttgtatt attaaaaga agtctgagat taacaataaa         600
ctaacactca tttggattca ctgcag                                              626

<210> SEQ ID NO 9
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 9
atacaagcca ctaggcat                                                       18

<210> SEQ ID NO 10
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 10
gattggccat gcaatgaggg aaaagg                                              26

<210> SEQ ID NO 11
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 11
cuacuacuac uactcgagac aaagccttta gcctatg                                  37

<210> SEQ ID NO 12
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 12
caucaucauc auggatccca tgtctctcta tgcaag                                   36

<210> SEQ ID NO 13
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 13
acgaattcct cgaggtaaat taaattgtgc ctgc                                     34

<210> SEQ ID NO 14
<211> LENGTH: 33
```

```
<212> TYPE: DNA
<213> ORGANISM: Artificial Sequence
<220> FEATURE:
<223> OTHER INFORMATION: Synthetic Oligonucleotide

<400> SEQUENCE: 14
gcgagatcta tcgatctgtg tcaaagtata aac                          33

<210> SEQ ID NO 15
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 15
gatcgatgcc cggggtaata attttttgtgt                             30

<210> SEQ ID NO 16
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 16
cacgcctcga gtgttcaatt caatcaatg                               29

<210> SEQ ID NO 17
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 17
cactcgagtt agttcatact ggct                                    24

<210> SEQ ID NO 18
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 18
cgcatcgatt gcaaaatcca tcaaa                                   25

<210> SEQ ID NO 19
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 19
cuacuacuac uactcgagcg taaatagtgg gtgaacac                     38

<210> SEQ ID NO 20
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 20
```

-continued caucaucauc auctcgagga attcgtccat tttagtacac c                41

<210> SEQ ID NO 21
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 21
cuacuacuac uactcgaggc gcgtacattt tattgctta                  39

<210> SEQ ID NO 22
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 22
caucaucauc auctcgagga attctgcagt gaatccaaat g                41

<210> SEQ ID NO 23
<211> LENGTH: 1734
<212> TYPE: DNA
<213> ORGANISM: Glycine max

<400> SEQUENCE: 23
actatagggc acgcgtggtc gacggcccgg gctggtcctc ggtgtgactc agccccaagt    60
gacgccaacc aaacgcgtcc taactaaggt gtagaagaaa cagatagtat ataagtatac   120
catataagag gagagtgagt ggagaagcac ttctcctttt tttttctctg ttgaaattga   180
aagtgttttc cgggaaataa ataaaataaa ttaaaatctt acacactcta ggtaggtact   240
tctaatttaa tccacacttt gactctatat atgttttaaa ataattata atgcgtactt     300
acttcctcat tatactaaat ttaacatcga tgattttatt ttctgtttct cttctttcca   360
cctacataca tcccaaaatt tagggtgcaa ttttaagttt attaacacat gttttagct    420
gcatgctgcc tttgtgtgtg ctcaccaaat tgcattcttc tctttatatg ttgtatttga   480
attttcacac catatgtaaa caagattacg tacgtgtcca tgatcaaata caaatgctgt   540
cttatactgg caatttgata aacagccgtc cattttttct ttttctcttt aactatatat   600
gctctagaat ctctgaagat tcctctgcca tcgaatttct ttcttggtaa caacgtcgtc   660
gttatgttat tattttattc tatttttatt ttatcatata tatttcttat tttgttcgaa   720
gtatgtcata ttttgatcgt gacaattaga ttgtcatgta ggagtaggaa tatcacttta   780
aaacattgat tagtctgtag gcaatattgt cttcttttc ctcctttatt aatatatttt    840
gtcgaagttt taccacaagg ttgattcgct ttttttgtcc ctttctcttg ttcttttac    900
ctcaggtatt ttagtctttc atggattata agatcactga gaagtgtatg catgtaatac   960
taagcaccat agctgttctg cttgaattta tttgtgtgta aattgtaatg tttcagcgtt  1020
ggctttccct gtagctgcta caatggtact gtatatctat tttttgcatt gttttcattt  1080
tttcttttac ttaatcttca ttgctttgaa attaataaaa caatataata tagtttgaac  1140
tttgaactat tgcctattca tgtaattaac ttattcactg actcttattg ttttttctggt  1200
agaattcatt ttaaattgaa ggataaaatta agaggcaata cttgtaaatt gacctgtcat  1260
aattacacag gaccctgttt tgtgcctttt tgtctctgtc tttggttttg catgttagcc  1320
tcacacagat atttagtagt tgttctgcat acaagcctca cacgtatact aaaccagtgg  1380

```
acctcaaagt catggcctta cacctattgc atgcgagtct gtgacacaac ccctggtttc    1440
catattgcaa tgtgctacgc cgtcgtcctt gtttgtttcc atatgtatat tgataccatc    1500
aaattattat atcatttata tggtctggac cattacgtgt actctttatg acatgtaatt    1560
gagtttttta attaaaaaaa tcaatgaaat ttaactacgt agcatcatat agagataatt    1620
gactagaaat ttgatgactt attctttcct aatcatattt tcttgtattg atagccccgc    1680 tgtcccttt aaactcccga gagagtataa aactgcatcg aatattacaa gatg           1734
```

<210> SEQ ID NO 24
<211> LENGTH: 405
<212> TYPE: DNA
<213> ORGANISM: Glycine max

<400> SEQUENCE: 24

```
gtatgatgct aaattaaatt gtgcctgcac cccaggatat ttcatgtggg attcatcatt      60
tattgaggaa aactctccaa attgaatcgt gcatttatat ttttttttcca tttctagatt   120 tcttgaaggc ttatggtata ggcacctaca attatcagca cttctctcta ttgataaaca    180
attggctgta ataccacagt agagaacgat cacaacattt tgtgctggtt acctttgtt    240 ttatggtcat gatttcactc tctctaatct gtcacttccc tccattcatt ttgtacttct    300 catattttc acttcctggt tgaaaattgt agttctcttg gtacatacta gtattagaca    360
ttcagcaaca caactgaac tgaacttctt tatactttga cacag                      405
```

<210> SEQ ID NO 25
<211> LENGTH: 98
<212> TYPE: DNA
<213> ORGANISM: Glycine max

<400> SEQUENCE: 25

```
gtgagtgatt ttttgacttg gaagacaaca acacattatt attataatat ggttcaaaac     60
aatgactttt tctttatgat gtgaactcca ttttttag                              98
```

<210> SEQ ID NO 26
<211> LENGTH: 115
<212> TYPE: DNA
<213> ORGANISM: Glycine max

<400> SEQUENCE: 26

```
gtaactaaat tactcctaca ttgttacttt ttcctccttt ttttattat ttcaattctc      60 caattggaaa tttgaaatag ttaccataat tatgtaattg tttgatcatg tgcag          115
```

<210> SEQ ID NO 27
<211> LENGTH: 778
<212> TYPE: DNA
<213> ORGANISM: Glycine max
<220> FEATURE:
<221> NAME/KEY: misc_feature
<222> LOCATION: (1)...(778)
<223> OTHER INFORMATION: n = A,T,C or G

<400> SEQUENCE: 27

```
atacaagcca ctaggcatgg taaattaaat tgtgcctgca cctcgggata tttcatgtgg      60
ggttcatcat atttgttgag gaaaagaaac tcccgaaatt gaattatgca tttatatatc    120
ctttttcatt tctagatttc ctgaaggctt aggtgtaggc acctagctag tagctacaat    180
atcagcactt ctctctattg ataaacaatt ggctgtaatg ccgcagtaga ggacgatcac    240
```

```
aacatttcgt gctggttact ttttgttta   tggtcatgat ttcactctct ctaatctctc    300
cattcatttt gtagttgtca ttatctttag  atttttcact acctggttta aaattgaggg    360
attgtagttc tgttggtaca tattacacat  tcagcaaaac aactgaaact caactgaact    420
tgtttatact ttgacacagg gtctagcaaa  ggaaacaaca atgggaggta gaggtcgtgt    480
ggccaaagtg gaagttcaag ggaagaagcc  tctctcaagg gttccaaaca caaagccacc    540
attcactgtt ggccaactca agaaagcaat  tccaccacac tgctttcagc gctccctcct    600
cacttcattc tcctatgttg tttatgacct  ttcatttgcc ttcattttct acattgccac    660
cacctacttc cacctccttc ctcaaccctt  ttccctcatt gcatggccaa tcaagccgaa    720
ttctgcagat atccatcaca tggcggcggn  tggngnaggn ntntanaggg cccaattc      778
```

<210> SEQ ID NO 28
<211> LENGTH: 148
<212> TYPE: DNA
<213> ORGANISM: Glycine max

<400> SEQUENCE: 28

```
gtaatctcac tctcacactt tctttataca  tcgcacacca gtgtgggtta tttgcaacct     60
acaccgaagt aatgccctat aattaatggg  gttaacacat gtccaagtcc aatattttgt    120
tcacttattt gaacttgaac atgtgtag                                        148
```

<210> SEQ ID NO 29
<211> LENGTH: 361
<212> TYPE: DNA
<213> ORGANISM: Glycine max

<400> SEQUENCE: 29

```
gtatcccatt taacacaatt tgtttcatta  acatttaag agaatttttt tttcaaaata      60
gttttcgaaa ttaagcaaat accaagcaaa  ttgttagatc tacgcttgta cttgttttaa   120
agtcaaattc atgaccaaat tgtcctcaca  agtccaaacc gtccactatt ttattttcac   180
ctactttata gcccaatttg tcatttggtt  acttcagaaa agagaacccc atttgtagta   240
aatatattat ttatgaatta tggtagtttc  aacataaaac atatttatgt gcagttttgc   300
catccttcaa aagaagatag aaacttactc  catgttactc tgtctatatg taatttcaca   360
g                                                                    361
```

<210> SEQ ID NO 30
<211> LENGTH: 36
<212> TYPE: DNA
<213> ORGANISM: Glycine max

<400> SEQUENCE: 30

```
gcgatcgatg tatgatgcta aattaaattg tgcctg                               36
```

<210> SEQ ID NO 31
<211> LENGTH: 30
<212> TYPE: DNA
<213> ORGANISM: Glycine max

<400> SEQUENCE: 31

```
gcggaattcc tgtgtcaaag tataaagaag                                      30
```

<210> SEQ ID NO 32
<211> LENGTH: 19
<212> TYPE: DNA
<213> ORGANISM: Glycine max

```
<400> SEQUENCE: 32
catgctttct gtgcttctc                                                    19

<210> SEQ ID NO 33
<211> LENGTH: 19
<212> TYPE: DNA
<213> ORGANISM: Glycine max

<400> SEQUENCE: 33
gttgatccaa ccatagtcg                                                    19
```

NUCLEIC ACID SEQUENCES AND METHODS OF USE FOR THE PRODUCTION OF PLANTS WITH MODIFIED POLYUNSATURATED FATTY ACIDS

This application claims priority under 35 U.S.C. § 120 and is a continuation of U.S. application Ser. No. 09/638,508, filed Aug. 11, 2000 now abandoned, which application claims the benefit under 35 U.S.C. § 119 of U.S. Provisional Application Ser. No. 60/151,224 filed Aug. 26, 1999 and U.S. Provisional Application Ser. No. 60/172,128 filed Dec. 17, 1999. U.S. application Ser. No. 09/638,508 is herein incorporated by reference in its entirety.

INCORPORATION OF SEQUENCE LISTING

A paper copy of the Sequence Listing for application entitled "Nucleic Acid Sequences and Methods of Use for the Production of Plants with Modified Polyunsaturated Fatty Acids" is herein incorporated by reference.

TECHNICAL FIELD

The present invention is directed to nucleic acid sequences and constructs, and methods related thereto.

BACKGROUND

Plant oils are used in a variety of applications. Novel vegetable oils compositions and/or improved means to obtain oils compositions, from biosynthetic or natural plant sources, are needed. Depending upon the intended oil use, various different fatty acid compositions are desired.

One means postulated to obtain such oils and/or modified fatty acid compositions is through the genetic engineering of plants. However, it is necessary to identify the appropriate nucleic acid sequences which are capable of producing the desired phenotypic result, regulatory regions capable of directing the correct application of such sequences, and the like.

Higher plants appear to synthesize fatty acids via a common metabolic pathway (fatty acid synthetase pathway). In developing seeds, where fatty acids are attached to glycerol backbones, forming triglycerides, for storage as a source of energy for further germination, the FAS pathway is located in the proplastids. The first committed step is the formation of acetyl-ACP (acyl carrier protein) from acetyl-CoA and ACP catalyzed by the enzyme, acetyl-CoA:ACP transacylase (ATA). Elongation of acetyl-ACP to 16- and 18-carbon fatty acids involves the cyclical action of the following sequence of reactions: condensation with a two-carbon unit from malonyl-ACP to form a β-ketoacyl-ACP (β-ketoacyl-ACP synthase), reduction of the keto-function to an alcohol (β-ketoacyl-ACP reductase), dehydration to form an enoyl-ACP (β-hydroxyacyl-ACP dehydrase), and finally reduction of the enoyl-ACP to form the elongated saturated acyl-ACP (enoyl-ACP reductase). β-ketoacyl-ACP synthase I, catalyzes elongation up to palmitoyl-ACP (C16:0), whereas β-ketoacyl-ACP synthase II catalyzes the final elongation to stearoyl-ACP (C18:0). Common plant unsaturated fatty acids, such as oleic, linoleic and a-linolenic acids found in storage triglycerides, originate from the desaturation of stearoyl-ACP to form oleoyl-ACP (C18:1) in a reaction catalyzed by a soluble plastid Δ-9 desaturase (also often referred to as "stearoyl-ACP desaturase"). Molecular oxygen is required for desaturation in which reduced ferredoxin serves as an electron co-donor. Additional desaturation is effected sequentially by the actions of membrane bound Δ-12 desaturase and Δ-15 desaturase. These "desaturases" thus create mono- or polyunsaturated fatty acids respectively.

Obtaining nucleic acid sequences capable of producing a phenotypic result in FAS, desaturation and/or incorporation of fatty acids into a glycerol backbone to produce an oil is subject to various obstacles including but not limited to the identification of metabolic factors of interest, choice and characterization of an enzyme source with useful kinetic properties, purification of the protein of interest to a level which will allow for its amino acid sequencing, utilizing amino acid sequence data to obtain a nucleic acid sequence capable of use as a probe to retrieve the desired DNA sequence, and the preparation of constructs, transformation and analysis of the resulting plants.

Thus, additional nucleic acid targets and methods for modifying fatty acid compositions are needed. In particular, constructs and methods to produce a variety of ranges of different fatty acid compositions are needed.

SUMMARY OF THE INVENTION

The present invention is generally directed to genomic desaturase polynucleotides, and in particular to genomic desaturase polynucleotides which encode enzymes that catalyze the insertion of a double bond into a fatty acyl moiety at the twelfth (Δ12 desaturase or fad2) or fifteenth (Δ15 desaturase or fad3) carbon position in a fatty acyl chain as counted from the carboxyl terminus. Further, the present invention provides isolated non-coding regions of such genomic polynucleotide sequences, particularly including the introns, and promoter regions. Specific oligonucleotides are provided which include partial or complete sequences which are derived from Δ12 and Δ15 desaturase promoter and intron sequences. Although the sequences disclosed herein are obtained from soybean plants, it is contemplated that additional sequences can be derived from intron and promoter regions of desaturase genomic polynucleotide sequences which are homologous or have identity to the soybean desaturase sequences. Such additional desaturase sequences can be obtained using standard methods described below from a variety of plant sources, in particular oilseed crops.

It is also an aspect of the present invention to provide recombinant DNA constructs which can be used for the modification of the fatty acid composition in a plant and in particular, to modify the transcription or transcription and translation (expression) of desaturase genes or proteins, such as Δ12 and Δ15 desaturase. The invention is particularly directed to DNA constructs which include sequences which are derived from the intron or promoter regions of a genomic clone wherein said sequences are in a sense or antisense orientation in a DNA construct. These DNA constructs are then used to transform or transfect host cells to produce plants with modified levels of fatty acids, particularly modified levels of oleic, linoleic and linolenic acid. It is particularly contemplated to provide constructs and methods for down regulating Δ12 and Δ15 desaturase gene expression, so as to increase the levels of oleic acid and to decrease the levels of linoleic acid and linolenic acid. It is particularly contemplated to alter the fatty acid composition in seed tissue of oilseed crops.

The modified plant cells, plants, seeds and oils obtained by the expression of the Δ12 and Δ15 desaturase polynucleotides are also considered part of the invention. Further, it is contemplated to produce oil compositions with specific relative levels of each fatty acid. One preferred embodiment comprises at least about 80-85% oleic acid, no more than about 1-2% linoleic acid, and no more than about 1-3% linolenic acid; and a second preferred embodiment comprising at least about 50-75% oleic acid, at least about 10-30% linoleic acid, and no more than about 3% linolenic acid.

DETAILED DESCRIPTION OF THE INVENTION

The present invention is directed to genomic desaturase sequences, particularly the isolated non-coding sequences from genomic fatty acid desaturase nucleic acid sequences from host cell sources. A desaturase sequence of this invention includes any nucleic acid genomic sequence, including all non-coding regions, encoding amino acids from a source, such as a protein, polypeptide or peptide, obtainable from a cell source, which is capable of catalyzing the insertion of a double bond into a fatty acyl moiety in a plant host cell, i.e., in vivo, or in a plant cell-like environment, i.e. in vitro. As will be described in more detail below, specific genomic polynucleotide sequences encoding enzymes which add double bonds at the twelfth (Δ12 desaturase) and fifteenth (Δ15 desaturase) carbon positions in a fatty acyl chain as counted from the carboxyl terminus are provided. In addition, provided herein are specific non-coding regions of such genomic sequences.

The term "non-coding" refers to sequences of polynucleotides that do not encode part or all of an expressed protein. Non-coding sequences include but are not limited to introns, promoter regions, and 5' untranslated regions.

The term "intron" as used herein refers to the normal sense of the term as meaning a segment of polynucleotides; usually DNA, that does not encode part or all of an expressed protein.

The term "exon" as used herein refers to the normal sense of the term as meaning a segment of polynucleotides, usually DNA, that encodes part or all of an expressed protein.

Thus, the term "intron" refers to gene regions that are transcribed into RNA molecules, but which are spliced out of the RNA before the RNA is translated into a protein. As contrasted to the term "exon" which refers to gene regions that are transcribed into RNA and subsequently translated into proteins.

As set forth in detail in the sequence listing and the examples, genomic Δ12 desaturase and Δ15 desaturase sequences and intron and promoter regions obtained from such sequences are provided herein. In particular, two Δ12 desaturase genomic clones were identified and are set forth in SEQ ID NOS:1 and 23. A single Δ15 desaturase genomic clone was identified and is set forth in SEQ ID NO:3. A single intron region was obtained from each of the Δ12 desaturase genomic clones with the sequences provided in SEQ ID NOS:2 and 24, respectively. The promoter region from each of the Δ12 desaturase genomic clones are respectively included in SEQ ID NO:1 (base pairs 1-1094) and SEQ ID NO:23 (base pairs 1-1704). The Δ15 desaturase included seven introns in the coding region (set forth as SEQ ID NOs:4, 5, 6, 7, 8, 25 and 26). In addition, preliminary results suggest that there is an additional intron within the 5' untranslated region.

Although the sequences described herein are obtained from soybean, it is contemplated that intron and promoter regions can be obtained from desaturase genomic polynucleotide sequences which are homologous or have identity to the soybean desaturase sequences. In particular, sequences can be obtained from other plant sources and particularly from oilseed crops. Such genomic sequences can be obtained using standard methods, certain of which are described below.

The sequences of the present invention can be used to modify the fatty acid composition in a plant (see Example 3 and Table I). In particular, it is shown that sense and antisense suppression can be used to obtain broad ranges in the levels of oleic, linoleic and linolenic acid. In particular, it is shown that levels of oleic acid can range from about 26 to 80%, levels of linoleic acid can range from about 2.97 to 49.92% and levels of linolenic acid can range from about 3.38 to 8.81%. However, these are merely representative of the broad range that be can achieved. Moreover, it is contemplated that combinations of the sequences could be used to achieve additional fatty acid compositions. Certain compositions are preferred based on the intended use of the oil.

One preferred composition includes at least about 50-75% oleic acid, at least about 10-30% linoleic acid and no more than about 3% linolenic acid. A particularly preferred embodiment includes at least about 60-70% oleic acid, at least about 15-20% linoleic acid and no more than about 3% linolenic acid.

Although the examples set forth herein utilize sense or antisense suppression to downregulate the gene of interest, it is contemplated that other means of modifying gene expression can be used. In particular, it is contemplated that gene expression can be down regulated using DNA binding proteins which can be designed to specifically bind to the non-coding regions identified herein or that ribozymes can be designed to cleave such non-coding regions. In addition, as described below, other methods of downregulation of gene expression which are well known in the art are contemplated and can be used with the sequences of the present invention.

Isolated Polynucleotides, Proteins, and Polypeptides

A first aspect of the present invention relates to isolated desaturase polynucleotides. The polynucleotide sequences of the present invention include isolated polynucleotides that are obtainable from genomic nucleic acid sequences.

The invention provides a polynucleotide sequence identical over its entire length to each sequence as set forth in the Sequence Listing. The polynucleotide includes non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

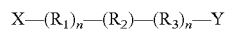

wherein, at the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the group set forth in the Sequence Listing and preferably SEQ ID NOs: 1-8, and 23-29. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer.

Further preferred embodiments of the invention that are at least 50%, 60%, or 70% identical over their entire length to a polynucleotide of the invention, and polynucleotides that are complementary to such polynucleotides. More preferable are polynucleotides that comprise a region that is at least 80% identical over its entire length to a polynucleotide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that are obtained from genomic polynucleotide sequences and set forth in the Sequence Listing.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5× SSC (150 mM NaCl, 15 mM trisodium citrate), 50 mM sodium phosphate (pH 7.6), 5× Denhardt's solution, 10% dextran sulfate, and 20 micrograms/milliliter denatured, sheared salmon sperm DNA, followed by washing the hybridization support in 0.1× SSC at approximately 65° C. Other hybridization and wash conditions are well known and are exemplified in Sambrook, et al., Molecular Cloning: A Laboratory Manual, Second Edition, Cold Spring Harbor, N.Y. (1989), particularly Chapter 11.

The invention also provides a polynucleotide consisting essentially of a polynucleotide sequence obtainable by screening an appropriate library containing the complete gene for a polynucleotide sequence set forth in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

The region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a polynucleotide of the invention is then used to screen a library of cDNA, genomic DNA or mRNA to identify members of the library which hybridize to the probe. For example, synthetic oligonucleotides are prepared which correspond to the desaturase promoter and intron sequences. In particular, screening of cDNA libraries in phage vectors is useful in such methods due to lower levels of background hybridization.

Typically, a desaturase sequence obtainable from the use of nucleic acid probes will show 60-70% sequence identity between the target desaturase sequence and the encoding sequence used as a probe. However, lengthy sequences with as little as 50-60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20-50% deviation (i.e., 50-80% sequence homology) from the sequences used as probe. Oligonucleotide probes can be considerably shorter than the entire nucleic acid sequence encoding an desaturase enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related desaturase genes. Shorter probes are often particularly useful for polymerase chain reactions (PCR), especially when highly conserved sequences can be identified. (See, Gould, et al., *PNAS USA* (1989) 86:1934-1938).

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math,* 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology,* 12: 76-80 (1994); Birren, et al., *Genome Analysis, I*1: 543-559 (1997)). The BLAST X program is publicly available from NCBI and other sources (BLAST Manual, Altschul, S., et al., NCBI NLM NIH, Bethesda, Md. 20894; Altschul, S., et al., *J. Mol. Biol.,* 215:403-410 (1990)). The well known Smith Waterman algorithm can also be used to determine identity.

Parameters for polypeptide sequence comparison typically include the following:

Algorithm: Needleman and Wunsch *J. Mol. Biol.* 48:443-453 (1970)

Comparison matrix: BLOSSUM62 from Hentikoff and Hentikoff, *Proc. Natl. Acad. Sci USA* 89:10915-10919 (1992)

Gap Penalty: 12

Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:

Algorithm: Needleman and Wunsch, J. Mol. Biol. 48:443-453 (1970)

Comparison matrix: matches=+10; mismatches=+0

Gap Penalty: 50

Gap Length Penalty: 3

A program which can be used with these parameters is publicly available as the "gap" program from Genetics Computer Group, Madison Wis. The above parameters are the default parameters for nucleic acid comparisons.

For immunological screening, antibodies to the protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the encoded proteins When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual*, Second Edition (1989) Cold Spring Harbor Laboratory, Cold Spring Harbor, N.Y.)

Plant Constructs and Methods of Use

Of particular interest is the use of the polynucleotide sequences in recombinant DNA constructs to direct the transcription of the desaturase genomic sequences of the present invention in a host plant cell. The expression constructs generally comprise a promoter functional in a host plant cell operably linked to a nucleic acid sequence of the present invention and a transcriptional termination region functional in a host plant cell.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313:810-812; Rogers, U.S. Pat. No. 5,378,619). In addition, it may also be preferred to bring about expression of the sequences of the present invention in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res.* 1:209:219 (1991)), phaseolin, zein, soybean trypsin inhibitor, ACP, stearoyl-ACP desaturase, soybean α' subunit of β-conglycinin (soy 7s, (Chen et al., *Proc. Natl. Acad. Sci.,* 83:8560-8564 (1986))) and oleosin.

It may be advantageous to direct the localization of proteins conferring desaturase to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol. Biol. Rep.* 9:104-126; Clark et al. (1989) *J. Biol. Chem.* 264:17544-17550; della-Cioppa et al. (1987) *Plant Physiol.* 84:965-968; Romer et al. (1993) *Biochem. Biophys. Res Commun.* 196:1414-1421; and, Shah et al. (1986) *Science* 233:478-481.

Depending upon the intended use, the constructs may contain the entire genomic nucleic acid sequence or a particular non-coding region of such a sequence or a portion of such sequences. For example, where antisense inhibition of a given desaturase protein is desired, the entire sequence is not required. Furthermore, where desaturase sequences used in constructs are intended for use as probes, it maybe advantageous to prepare constructs containing only a particular portion of a desaturase sequence, for example a sequence which encodes a highly conserved desaturase region.

The skilled artisan will recognize that there are various methods for the inhibition of expression of endogenous sequences in a host cell. Such methods include, but are not limited to, antisense suppression (Smith, et al (1988) *Nature* 334:724-726), co-suppression (Napoli, et al. (1989) *Plant Cell* 2:279-289), ribozymes (PCT Publication WO 97/10328), combinations of sense and antisense (Waterhouse, et al. (1998) *Proc. Natl. Acad. Sci. USA* 95:13959-13964), promoter silencing (Park, et al. (1996) *Plant J.* 9(2):183-194), DNA binding proteins (Beerli, et al. (1997) *Proc. Natl. Acad. Sci. USA,* 95:14628-14633; and Liu, et al. (1998) *Proc. Natl. Acad. Sci. USA,* 94:5525-5530). Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the desaturase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the desaturase sequences directly from the host plant cell plastid. Such constructs and methods are known in the art and are generally described, for example, in Svab, et al. (1990) *Proc. Natl. Acad. Sci. USA* 87:8526-8530 and Svab and Maliga (1993) *Proc. Natl. Acad. Sci. USA* 90:913-917 and in U.S. Pat. No. 5,693,507.

A plant cell tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a desaturase nucleic acid sequence.

Plant expression or transcription constructs having a desaturase polynucleotide of the present invention as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledons and monocotyledons species alike and will be readily applicable to new and/or improved transformation and regulation techniques.

Of particular interest, is the use of plant desaturase promoter and/or intron constructs in plants to produce plants or plant parts, including, but not limited to leaves, stems, roots, reproductive, and seed, with a modified fatty acid composition. Of particular interest in the desaturase promoter and/or intron constructs is the use of the promoter and/or intron sequences of the Δ-12 and Δ-15 desaturase genomic sequences in sense or antisense orientations for the modification of fatty acid compositions in host cells.

The polynucleotides of the present invention can be used in the preparation of constructs for use in a variety of host cells. Host for use in the present invention include, but are not limited to plant cells, bacterial cells, fungal cells (including yeast), insect cells, and mammalian cells.

For example, to confirm the activity and specificity of the proteins encoded by the identified nucleic acid sequences as desaturase enzymes, in vitro assays can be performed in insect cell cultures using baculovirus expression systems. Such baculovirus expression systems are known in the art and are described by Lee, et al. U.S. Pat. No. 5,348,886, the entirety of which is herein incorporated by reference.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to *Agrobacterium* infection may be successfully transformed via tripartite or binary vector methods of *Agrobacterium* mediated transformation. In many instances, it will be desirable to have the construct bordered on one or both sides by T-DNA, particularly having the left and right borders, more particularly the right border. This is particularly useful when the construct-uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic heavy metal, toxin, etc. complementation providing prototrophy to an auxotrophic host, viral immunity or the like. Depending upon the host species the expression construct or components thereof are introduced, one or more markers may be employed, where different conditions for selection are used for the different hosts.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region(s) will be inserted into a broad host range vector capable of replication in *E. coli* and *Agrobacterium*, there being broad host range vectors described in the literature. Commonly used is pRK2 or derivatives thereof. See, for example, Ditta, et al., (*Proc. Nat. Acad Sci., U.S.A. (*1980) (77:7347-7351) and EPA 0 120 515, which are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride and Summerfelt (*Plant Mol. Biol.* (1990) 14:269-276), wherein the pRiHRI (Jouanin, et al., *Mol. Gen. Genet* (1985) 201:370-374) origin of replication is utilized and provides for added stability of the plant expression vectors in host *Agrobacterium* cells.

Included with the expression construct and the T-DNA will be one or more markers, which allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

For the alteration of unsaturated fatty acid production in a host cell, a second expression construct can be used in accordance with the present invention. For example, the desaturase expression construct can be introduced into a host cell in conjunction with a second expression construct having a nucleotide sequence for a protein involved in fatty acid biosynthesis.

There are several possible ways to obtain the plant cells of this invention which contain multiple expression constructs. Any means for producing a plant comprising a construct having a DNA sequence encoding the expression construct of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the desaturase expression construct, or alternatively, transformed plants, one expressing the desaturase construct and one expressing the second construct, can be crossed to bring the constructs together in the same plant.

The invention now being generally described, it will be more readily understood by reference to the following examples which are included for purposes of illustration only and are not intended to limit the present invention.

EXAMPLES

Example 1

Cloning of Desaturase Genomic Sequences

1A. Soybean Δ12 Desaturase (fad2-1)

The soybean fad 2-1A sequence was identified by screening a soybean genomic library using a soybean fad2-1 cDNA probe. Three putative soy fad 2-1 clones were identified and plaque purified. Two of the three soy fad 2-1 clones were ligated into pBluescript II KS+ (Stratagene) and sequenced. Both clones (14-1 and 11-12) were the same and matched the soy fad 2-1 cDNA exactly. The sequence of the entire fad2-1A clone is provided in SEQ ID NO: 1.

Prior to obtaining this full length clone, a portion of the fad2-1A genomic clone was PCR amplified using PCR primers designed from the 5' untranslated sequence (Primer 12506, 5'-ATACAA GCCACTAGGCAT-3', SEQ ID NO:9) and within the cDNA (Primer 11698: 5'-GATTGGCCATG-CAATGAGGGAAAAGG-3', SEQ ID NO:10. The resulting PCR product, which contained the fad2-1A intron, was cloned into the vector pCR 2.1 (Invitrogen) and sequenced. The soy fad 2-1A partial genomic clone (SEQ ID NO:27) and its intron region (SEQ ID NO:2) were identified by comparison to the soybean cDNA sequence using the Pustell comparison program in Macvector. The intron sequence begins after the ATG start codon, and is 420 bases long.

A second fad2-1 gene family member was also identified and cloned, and is referred to herein as fad2-1B. The soy fad 2-1B partial genomic clone (SEQ ID NO:23) (contains the promoter (base pairs 1-1704); 5'UTR (base pairs 1705-1782); intron#1 (base pairs 1786-2190); and a portion of the fad2-1B coding region (base pairs 1783-1785 and 2191-2463)) and its intron region (SEQ ID NO:24) were identified by comparison to the soybean cDNA sequence using the Pustell comparison program in Macvector. The intron sequence begins after the ATG start codon and is 405 bases long.

1B. Soybean Δ15 Desaturase (fad3)

The partial soybean fad 3 genomic sequence was PCR amplified from soybean DNA using primers 10632, 5'-CUACUACUACUACTCGAGACAAAGCCTT-TAGCCTATG-3' (SEQ ID NO:11), and 10633: 5'-CAU-CAUCAUCAUGGATCCCATGTCTCTCTATGCAAG-3' (SEQ ID NO:12). The Expand Long Template PCR system (Boehringer Mannheim) was used according to the manufacturers directions. The resulting PCR products were cloned into the vector pCR 2.1 (Invitrogen) and sequenced. The soy fad 3 partial genomic clone sequence and the intron regions were confirmed by comparisons to the soybean fad 3 cDNA sequence using the Pustell program in Macvector. From the identified partial genomic soybean fad3 sequence (SEQ ID NO:3), seven introns were identified (SEQ ID NO:4 (intron #1), SEQ ID NO:5 (intron #2); SEQ ID NO:6 (intron #3A), SEQ ID NO:7 (intron #4), SEQ ID NO:8 (intron #5), SEQ ID NO:25 (intron #3B) and SEQ ID NO:26 (intron #3C)). Intron #1 is 192 base pairs long and is located between positions 294 and 485, intron #2 is 348 base pairs long and is located between positions 576 and 923, intron #3A is 142 base pairs long and is located between positions 991and 1132, intron #3B is 98 base pairs long and is located between positions 1225 and 1322, intron #3C is 115 base pairs long and is located between positions 1509 and 1623, intron #4 is 1231 base pairs long and is located between positions 1705and 2935, and intron #5 is 626 base pairs long and is located between positions 3074 and 3699.

Example 2

Expression Constructs

The soybean fad2-1A intron sequence was amplified via PCR using the fad2-1A partial genomic clone (SEQ ID NO:27) as a template and primers 12701 (5'-ACGAATTC-CTCGAGGTAAA TTAAATTGTGCCTGC-3' (SEQ ID NO:13)) and 12702 (5'-GCGAGATCTATCG ATCTGTGT-CAAAGTATAAAC-3' (SEQ ID NO:14)). The resulting amplification products were cloned into the vector pCR 2.1 (Invitrogen) and sequenced. The soyfad2-1A intron was then cloned into the expression cassette, pCGN3892, in sense and antisense orientations. The vector pCGN3892 contains the soybean 7S promoter and a pea RBCS 3'. Both gene fusions were then separately ligated into pCGN9372, a vector that contains the CP4 gene regulated by the FMV promoter. The resulting expression constructs (PCGN5469 sense and pCGN5471 antisense) were used for transformation of soybean using biolistic methods described below.

The soybean fad2-1 B intron sequence was amplified via PCR using the fad2-1B partial genomic clone (SEQ ID NO:23) as a template and primers 13883 (5'-GCGATCGAT-GTATGATGCTAAATTAAATTGTGCCTG-3' (SEQ ID NO:30)) and 13876 (5'-GCGGAATTCCTGTCTCAAAG-TATAAAGAAG-3'(SEQ ID NO:31)). The resulting amplification products were cloned into the vector pCR 2.1 (Invitrogen) and sequenced. The soyfad2-1B intron was fused to the 3' end of the soy fad 2-1A intron in plasmids pCGN5468 (contains the soybean 7S promoter fused to the soy fad2-1A intron (sense) and a pea RBCS 3') or pCGN5470 (contains the soybean 7S promoter fused to the soy fad2-1A intron (antisense) and a pea RBCS 3') in sense or antisense orientation respectively. The resulting intron combo fusions were then ligated separately into pCGN9372, a vector that contains the CP4 gene regulated by the FMV promoter. The resulting expression constructs (pCGN5485, fad2-1A&B intron sense and pCGN5486, fad2-1A&B intron antisense) were used for transformation of soybean using biolistic methods described below.

Four of the seven introns identified from the soybean fad 3 genomic clone were PCR amplified using the soy fad 3 partial genomic clone as template and primers as follows: Intron #1, primers 12568: GATCGATGCCCGGGG-TAATAATTTTTGTGT (SEQ ID NO:15) and 12569: CACGCCTCGAGTGTTCAATTCAATCAATG (SEQ ID NO:16); Intron #2, primers 12514: 5'-CACTCGAGTTAGT-TCATACTGGCT (SEQ ID NO: 17) and 12515: 5'-CG-CATCGATTGCAAAATCCATCAAA (SEQ ID NO:18); Intron #4, primers 10926: 5'- CUACUACUACUACTC-GAGCGTAAATAGTGGGTGAACAC (SEQ ID NO:19) and 10927:5'-CAUCAUCAUCAUCTCGAGGAAT-TCGTCCATTTTAGTACACC (SEQ ID NO:20); Intron #5, primers 10928: 5'-CUACUACUACUACTCGAGGCGCGT ACATTTTATTGCTTA (SEQ ID NO:21) and 10929:5'-CAUCAUCAUCAUCT CGAGGAATTCTGCAGT-GAATCCAAATG (SEQ ID NO:22). The resulting PCR products for each intron were cloned into the vector pCR 2.1 (Invitrogen) and sequenced. Introns #1, #2, #4 and #5 were all ligated separately into the pCGN3892, in sense or antisense orientations. pCGN3892 contains the soybean 7S promoter and a pea RBCS 3'. These fusions were ligated into pCGN9372, a vector that contains the CP4 gene regulated by the FMV promoter for transformation into soybean. The resulting expression constructs (pCGN5455, fad3 intron#4 intron sense; pCGN5459, fad3 intron#4 intron antisense; pCGN5456, fad3 intron#5 intron sense; pCGN5460, fad3 intron#5 intron antisense; pCGN5466, fad3 intron#2 intron antisense; pCGN5473, fad3 intron#1 intron antisense;) were used for transformation of soybean using biolistic methods described below.

The soy fad3 Intron #3C and #4 were also PCR amplified from a second fad3 gene family member, herein referred to as fad3-1B. The soy fad3-1B introns #3C and #4 were PCR amplified from soybean DNA using the following primers, 5'CATGCTTTCTGTGCTTCTC 3' (SEQ ID NO:32) and, 5'GTTGATCCAACCATAGTCG 3' (SEQ ID NO:33). The PCR products were cloned into the vector pCR 2.1 (Invitrogen) and sequenced. The sequences for the soy fad3-1B introns #3C and #4 are provided in SEQ ID NOS:28 and 29.

Example 3

Plant Transformation and Analysis

Linear DNA fragments containing the expression constructs for sense and antisense expression of the Δ12 and Δ15 desaturase introns were stably introduced into soybean, (Asgrow variety A4922) by the method of McCabe, et. al. (1988) Bio/Technology 6:923-926. Transformed soybean plants were identified by selection on media containing, glyphosate.

Fatty acid compositions were analyzed from seed of soybean lines transformed with the intron expression constructs using gas chromatography T2 pooled seed and T2 single seed oil compositions demonstrate that the mono and polyunsaturated fatty acid compositions were altered in the oil of seeds from transgenic soybean lines as compared to that of the seed from non-transformed soybean. Table I provides a summary of results which were obtained using the described constructs. These data clearly show that sense and antisense expression of the non-coding regions of the desaturase gene results in the modification of the fatty acid compositions. The data also shows that introns can be used to obtain a variety of lines with varying fatty acid compositions. Selections can be made from such lines depending on the desired relative fatty acid composition. In addition, since each of the introns is able to modify the levels of each fatty acid to varying extents, it is contemplated that combinations of introns can be used depending on the desired compositions.

TABLE 1

|  | orientation | event | Oleic | Linoleic | Lino-lenic |
|---|---|---|---|---|---|
| Fad 2 | | | | | |
| wildtype (control) | | 5469-5 null T2 pool | 18.15% | 55.59% | 7.97% |
| | | 10 seed average | 13.89% | 55.89% | 9.067% |
| | | 5469-27 null T2 pool | 19.15% | 54.62% | 9.32% |
| | | A4922 | 15.75% | 56.1% | 8.75% |
| | | 5471-13 null T2 pool | 17.02% | 56.49% | 9.08% |
| | | 10 seed average | 13.86% | 56.14% | 9.49% |
| | | A4922 | 14.95% | 55.95% | 9.07% |
| full length cDNA (control) | sense | 5462-133 T2 pool | 84% | 2.17% | 1.55% |
| | | best 5462-133 T2 seed | 84% | 0.59% | 1.76% |
| intron 1 | sense | 5469-6 T2 pool | 29.93% | 46.53% | |
| | | 5469-8 T2 pool | 36.5% | 42.11% | 5.98% |
| | | best 5469-6 T2 seed | 44.41% | 29.34% | 6.68% |
| | | best 5469-8 T2 seed | 41.26% | 33.16% | 5.74% |
| | | 5469-14 T2 pool | 61.06% | 16.42% | 7.75% |
| | | 5469-20 T2 pool | 48.89% | 31.61% | 4.89% |
| | | 5469-22 T2 pool | 80% | 2.97% | 4.78% |
| | | best 5469-14 T2 seed | 62.21% | 11.97% | 8.81% |
| | | 5485-3 T2 pool | 63.54% | 14.09% | 7.32% |
| | | 5485-53 T2 pool | 47.58% | 27.64% | 7.81% |
| | antisense | 5471-8 T2 pool | 31.05% | 43.62% | 7.07% |
| | | 5471-2 T2 pool | 27.98% | 48.88% | 6.83% |
| | | 5471-26 T2 pool | 32.66% | 44.54% | 6.76% |
| | | best 5471-8 T2 seed | 57.4% | 23.37% | 5.73% |
| | | best 5471-2 T2 seed | 28.08% | 46.14% | 6.52% |
| | | best 5471-26 T2 seed | 43.3% | 34.15% | 5.6% |
| | | 5486-33 T2 pool | 32.37% | 43.66% | 6.87% |
| | | 5486-12 T2 pool | 27.32% | 46.97% | 6.4% |
| | | 5486-40 T2 pool | 26.79% | 48.72% | 6.55% |
| Fad 3 | | | | | |
| wildtype (control) | | 5473-7 null T2 pool | 15.65% | 56.74% | 9.55% |
| | | A4922 T2 pool | 19.84% | 56.79% | 7.48% |
| full length cDNA (control) | sense | 5464-50 T2 pool | 18.06% | 62.03% | 2.75% |
| | | best 5464-50 T2 seed | 17.08% | 62.44% | 1.72% |
| intron 1 | antisense | 5473-8 T2 pool | 33.47% | 45.97% | 5.54% |
| | | 5473-1 T2 pool | 33.34% | 42.67% | 7.59% |
| intron 2 | antisense | 5466-20 T2 pool | 28.43% | 48.83% | 6.37% |
| | | 5466-16 T2 pool | 27.61% | 49.92% | 5.96% |

TABLE 1-continued

| | orientation | event | Oleic | Linoleic | Lino-lenic |
|---|---|---|---|---|---|
| intron 4 | sense | 5455-19 T2 pool | 40.35% | 39.97% | 4.61% |
| | | 5455-10 T2 pool | 35.14% | 43.59% | 5.53% |
| | | 5455-57 T2 pool | 38.04% | 42.44% | 5.24% |
| | | 5455-76 T2 pool | 37.24% | 42.42% | 5.37% |
| | | 5455-107 T2 pool | 36.44% | 42.72% | 5.62% |
| | | best 5455-57 T2 seed | 45.36% | 35.55% | 4.92% |
| | | best 5455-76 T2 seed | 35.3% | 43.54% | 5.53% |
| | | best 5455-107 T2 seed | 45.56% | 34.85% | 5.12% |
| | antisense | 5459-2 T2 pool | 34.5% | 43.87% | 5.59% |
| | | 5459-6 T2 pool | 33.78% | 44.12% | 5.62% |
| | | 5459-20 T2 pool | 28.26% | 49.48% | 5.5% |
| | | best 5459-2 T2 seed | 61.45% | 23.45% | 3.38% |
| | | best 5459-6 T2 seed | 53.51% | 29.68% | 3.53% |
| | | best 5459-20 T2 seed | 30% | 50.55% | 4.15% |
| intron 5 | sense | 5456-38 T2 pool | 28.23% | 49.59% | 6.74% |
| | | 5456-62 T2 pool | 28.94% | 48.66% | 6.25% |
| | | best 5456-62 T2 seed | 29.5% | 43.69% | 5.4% |
| | antisense | 5460-9 T2 pool | 29.78% | 48.57% | 5.54% |
| | | 5460-21 T2 pool | 28.37% | 49.79% | 5.54% |
| | | best 5460-21 T2 seed | 35.18% | 40.52% | 5.33% |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understandings it will be obvious that certain changes and modifications may be practiced within the scope of the appended claims.

What is claimed is:

1. A soybean plant having a nucleic acid molecule comprising a promoter functional in a host plant cell operably linked to a polynucleotide that has at least 90% identity to SEQ ID NO: 2, a complement thereof, or a fragment of either, and a transcriptional termination region functional in said host plant cell, wherein a seed of said soybean plant exhibits a modified fatty acid composition that is about 26-80% oleic acid, about 2.97-49.92% linoleic acid, and about 3.38-8.81% linolenic acid.

2. The soybean plant according to claim 1, wherein said polynucleotide has at least 95% identity to SEQ ID NO: 2, a complement thereof, or a fragment of either.

3. The soybean plant according to claim 1, wherein said polynucleotide has at least 97% identity to SEQ ID NO: 2, a complement thereof, or a fragment of either.

4. The soybean plant according to claim 1, wherein said polynucleotide has at least 98% identity to SEQ ID NO: 2, a complement thereof, or a fragment of either.

5. The soybean plant according to claim 1, wherein said polynucleotide is SEQ ID NO: 2, a complement thereof, or a fragment of either.

6. The soybean plant according to claim 1, wherein said promoter is a heterologous promoter.

7. An soybean plant having a nucleic acid molecule comprising a promoter functional in a host plant cell operably linked to a polynucleotide that is a fad2 intron or complement thereof or fragment of either, wherein said polynucleotide has at least 90% identity to SEQ ID NO: 2, a complement thereof, or a fragment of either, and a transcriptional termination region functional in said host plant cell, wherein a seed of said soybean plant exhibits a modified fatty acid composition that is about 26-80% oleic acid, about 2.97-49.92% linoleic acid, and about 3.38-8.81% linolenic acid.

8. The soybean plant according to claim 7, wherein said polynucleotide is SEQ ID NO: 2, a complement thereof, or a fragment of either.

9. The soybean plant according to claim 7, wherein said promoter is a heterologous promoter.

10. A method of modifying the fatty acid composition in a seed of soybean plant comprising:
   growing an oilseed plant that has a nucleic acid molecule comprising a promoter functional in a host plant cell operably linked to a polynucleotide that is a fad2 intron or complement thereof or fragment of either, wherein said polynucleotide has at least 90% identity to SEQ ID NO: 2, a complement thereof, or a fragment of either, and a transcriptional termination region functional in said host plant cell, and
   harvesting said seed of said soybean plant, wherein said seed exhibits a modified fatty acid composition that is about 26-80% oleic acid, about 2.97-49.92% linoleic acid, and about 3.38-8.81% linolenic acid.

11. The soybean plant according to claim 10, wherein said polynucleotide has at least 95% identity to SEQ ID NO: 2, a complement thereof, or a fragment of either.

12. The soybean plant according to claim 10, wherein said polynucleotide has at least 97% identity to SEQ ID NO: 2, a complement thereof, or a fragment of either.

13. The soybean plant according to claim 10, wherein said polynucleotide has at least 98% identity to SEQ ID NO: 2, a complement thereof, or a fragment of either.

14. The soybean plant according to claim 10, wherein said polynucleotide is SEQ ID NO: 2, a complement thereof, or a fragment of either.

15. The soybean plant according to claim 10, wherein said promoter is a heterologous promoter.

16. The soybean plant according to claim 1, wherein said polynucleotide has at least 99% identity to SEQ ID NO: 2, a complement thereof, or fragment of either.

17. The soybean plant according to claim 7, wherein said polynucleotide has at least 95% identity to SEQ ID NO: 2, a complement thereof, or a fragment of either.

18. The soybean plant according to claim 7, wherein said polynucleotide has at least 97% identity to SEQ ID NO: 2, a complement thereof, or a fragment of either.

19. The soybean plant according to claim 7, wherein said polynucleotide has at least 98% identity to SEQ ID NO: 2, a complement thereof, or a fragment of either.

20. The soybean plant according to claim 7, wherein said polynucleotide has at least 99% identity to SEQ ID NO: 2, a complement thereof, or a fragment of either.

21. The soybean plant according to claim 10, wherein said polynucleotide has at least 99% identity to SEQ ID NO: 2, a complement thereof, or a fragment of either.

22. The soybean plant according to claim 1, wherein said polynucleotide is capable of suppressing fad2.

23. The soybean plant according to claim 7, wherein said polynucleotide is capable of suppressing fad2.

24. The soybean plant according to claim 10, wherein said polynucleotide is capable of suppressing fad2.

* * * * *

UNITED STATES PATENT AND TRADEMARK OFFICE
CERTIFICATE OF CORRECTION

PATENT NO.        : 7,256,329 B2
APPLICATION NO.   : 10/606772
DATED             : August 14, 2007
INVENTOR(S)       : Joanne Fillatti et al.

It is certified that error appears in the above-identified patent and that said Letters Patent is hereby corrected as shown below:

Col. 38, line 24, change "soybean plant according to" to --method according to--;

line 27, change "soybean plant according to" to --method according to--;

line 30, change "soybean plant according to" to --method according to--;

line 33, change "soybean plant according to" to --method according to--;

line 36, change "soybean plant according to" to --method according to--;

line 53, change "soybean plant according to" to --method according to--;

line 60, change "soybean plant according to" to --method according to--.

Signed and Sealed this

Twenty-fifth Day of November, 2008

JON W. DUDAS
*Director of the United States Patent and Trademark Office*